United States Patent
Sherman

(10) Patent No.: US 6,194,002 B1
(45) Date of Patent: Feb. 27, 2001

(54) PHARMACEUTICAL COMPOSITION COMPRISING BUPROPION HYDROCHLORIDE AND FUMARIC ACID

(76) Inventor: Bernarad Charles Sherman, 50 Old Colony Road, Willowdale, Ontario (CA), M2L 2K1

(*) Notice: Subject to any disclaimer, the term of this patent is extended or adjusted under 35 U.S.C. 154(b) by 0 days.

(21) Appl. No.: 09/368,586

(22) Filed: Aug. 5, 1999

(30) Foreign Application Priority Data

Aug. 21, 1998 (CA) .................................................. 2244097

(51) Int. Cl.⁷ ....................................................... A61K 9/20
(52) U.S. Cl. ........................... 424/464; 424/465; 514/970; 514/784
(58) Field of Search ...................................... 424/464, 465, 424/489, 451, 452

(56) References Cited

U.S. PATENT DOCUMENTS 5,358,970   10/1994   Ruff et al. ............................ 514/649

OTHER PUBLICATIONS

Hart, Organic Chemistry, 8th, Ed., p. 274, Jan. 1991.*

* cited by examiner

*Primary Examiner*—James M. Spear
(74) *Attorney, Agent, or Firm*—Nixon & Vanderhye P.C.

(57) ABSTRACT

A pharmaceutical composition in solid dosage form comprising bupropion hydrochloride as active drug and fumaric acid as stabilizer.

4 Claims, No Drawings

PHARMACEUTICAL COMPOSITION COMPRISING BUPROPION HYDROCHLORIDE AND FUMARIC ACID

BACKGROUND OF THE INVENTION

Bupropion hydrochloride is a well-known antidepressant. It is sold in the United States by Glaxo Wellcome Inc. as prompt release tablets under the tradename WELLBUTRIN® and sustained release tablets under the tradename, WELLBUTRIN SR®.

Bupropion hydrochloride is known to be relatively unstable, such that tablets containing bupropion hydrochloride will degrade at an unacceptably high rate unless the tablets are made by a method or using ingredients which result in improved stability.

U.S. Pat. No. 5,358,970 discloses stabilization of bupropion hydrochloride by including in the tablets a stabilizer. The specific stabilizers disclosed are L-cysteine hydrochloride, glycine hydrochloride, ascorbic acid, malic acid, sodium metabisulfite, isoascorbic acid, citric acid, and L-cysteine hydrochloride. L-cysteine hydrochloride and glycerin hydrochloride are said to be most preferred. All of the examples in U.S. Pat. No. 5,358,970 use L-cysteine hydrochloride or glycine hydrochloride as the stabilizer, and, in each example, the process of manufacture includes the steps of dissolving the stabilizer in water and alcohol, using the solution to granulate the bupropion hydrochloride and other ingredients, and then drying the wet mass.

Such a process has the disadvantage of requiring the use of water and alcohol, and requiring the steps of preparing the solution, using the solution to granulate powder, and drying the wet granulated material.

The object of the present invention is to enable stabilization of compositions comprising bupropion hydrochloride by using a stabilizer that is effective when added in dry form, so as to eliminate the need to use water, alcohol or any other solvent, and thus also eliminate the steps of preparing a solution, using the solution to granulate powder, and drying.

DESCRIPTION OF THE INVENTION

It has been found that the inclusion of fumaric acid as an ingredient in solid compositions comprising bupropion hydrochloride results in improved stability, even if the ingredients are mixed in dry form without use of water, alcohol or any other solvent.

Compositions within the scope of the present invention will thus be solid compositions (such as tablets or capsules) comprising bupropion hydrochloride and fumaric acid. A preferred ratio of fumaric acid to bupropion hydrochloride by weight is from about 0.05 to about 2.0. A more preferred ratio is from about 0.1 to about 1.2 and most preferred ratio is from about 0.2 to about 0.8.

Solid compositions in the form of tablets, for example, can be made simply by mixing bupropion hydrochloride and fumaric acid, along with other usual tabletting ingredients, and then compressing the mixture into tablets on a tablet process.

The other usual tabletting ingredients may include and will preferably include a binder, such as, for example, microcrystalline cellulose or hydroxypropyl methylcellulose; a lubricant such as, for example, magnesium stearate or stearic acid, and a glidant such as, for example, colloidal silicon dioxide.

If the flowability of the mixed powder is not adequate for direct compression into tablets, the mixture may be compacted, following which the compacted material will be ground up into free flowing granules. These granules will then be compressed into tablets on a tablet press.

The following examples are representative of the invention, but not limiting.

Ingredients were mixed in proportions as follows:

|  | Example 1 | Example 2 | Example 3 | Example 4 |
| --- | --- | --- | --- | --- |
| Bupropion hydrochloride | 100 | 100 | 100 | 100 |
| Hydroxypropyl methylcellulose | 92 | 80 | 70 | 60 |
| Fumaric acid | 0 | 12 | 22 | 32 |
| Stearic acid | 7.6 | 7.6 | 7.6 | 7.6 |
| Colloidal silicon dioxide | 6.4 | 0.4 | 0.4 | 0.4 |
|  | 200 | 200 | 200 | 200 |

In each case the powder mixture was compacted, the compacted material was ground up into granules, and the granules were recompressed on a tablet press into tablets of net weight 200 mg each. Each tablet thus contained 100 mg of bupropion hydrochloride, and the amount of fumaric acid per tablet was nil in example 1, 12 mg in example 2, 22 mg in example 3, and 32 mg in example 4.

The tablets of all 4 examples were stored for a period of two weeks at 40° C. and 75% relative humidity, this condition of elevated temperature and humidity being known to cause accelerated degradation of bupropion hydrochloride.

At the end of the two week period, the tablets were analyzed to determine the total amount of degradation products as a percentage of the initial amount of bupropion hydrochloride. The total amount of degradation products was found to be 5.1% for example 1, 1.79% for example 2, 0.78% for example 3, and 0.55% for example 4.

It thus can be seen that the inclusion of fumaric acid in the tablets decreases the rate of degradation. Furthermore, the rate of degradation decreases with increased amount of fumaric acid. In example 4, in which the ratio of fumaric acid to bupropion hydrochloride is 0.32, the rate of degradation is acceptably low, and it appears that there is thus little to be gained by using substantially above this level of fumaric acid. It is thus concluded that the most preferred ratio of fumaric acid to bupropion hydrochloride is about 0.32, or from about 0.2 to about 0.8.

What is claimed is:

1. A pharmaceutical composition in solid form comprising bupropion hydrochloride and fumaric acid, wherein the ratio of fumaric acid to bupropion hydrochloride by weight is from about 0.05 to about 2.0.

2. A composition as in claim 1, wherein the ratio of fumaric acid to bupropion hydrochloride by weight is from about 0.1 to about 1.2.

3. A composition as in claim 1, wherein the ratio of fumaric acid to bupropion hydrochloride by weight is from about 0.2 to about 0.8.

4. A composition as in claim 1 in the form of a tablet.

* * * * *